(12) United States Patent
Karakasoglu et al.

(10) Patent No.: US 6,213,955 B1
(45) Date of Patent: *Apr. 10, 2001

(54) APPARATUS AND METHOD FOR BREATH MONITORING

(75) Inventors: Ahmet Karakasoglu, San Francisco; Karl S. Johnson, Palo Alto; George D. Hermann, Portola Valley, all of CA (US)

(73) Assignee: Sleep Solutions, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/169,776

(22) Filed: Oct. 8, 1998

(51) Int. Cl.[7] ........................................ A61B 5/00
(52) U.S. Cl. .................. 600/529; 600/538; 128/204.23
(58) Field of Search .................. 600/529–538, 600/481, 500, 300; 128/897, 898

(56) References Cited

U.S. PATENT DOCUMENTS

| 4,129,125 |   | 12/1978 | Lester et al. ............... 128/715 X |
|-----------|---|---------|----------------------------------------|
| 4,802,485 | * | 2/1989  | Bowers et al. ................... 600/483 |
| 4,862,144 |   | 8/1989  | Tao ........................... 128/721 X |
| 4,956,867 |   | 9/1990  | Zurek et al. .                         |
| 5,046,491 | * | 9/1991  | Derrick ......................... 600/529 |
| 5,385,144 |   | 1/1995  | Yamanishi et al. ............. 128/633 X |
| 5,404,885 | * | 4/1995  | Sheehan et al. .................. 600/529 |
| 5,522,382 | * | 6/1996  | Sullivan et al. .............. 128/204.23 |
| 5,671,733 | * | 9/1997  | Raviv et al. ...................... 600/529 |
| 5,704,345 | * | 1/1998  | Berthon-Jones .............. 128/204.23 |
| 5,797,852 | * | 8/1998  | Karakasoglu ................... 600/529 |
| 5,803,066 | * | 9/1998  | Rapoprt et al. .................... 600/529 |

* cited by examiner

Primary Examiner—Cary O'Connor
Assistant Examiner—Michael Astorino
(74) Attorney, Agent, or Firm—Flehr Hohbach Test Albritton & Herbert LLP

(57) ABSTRACT

Apparatus for measuring respiratory air flow from the nostrils of the nose and/or the mouth of a patient comprising a device positioned in the vicinity of the nose and/or mouth of the patient and having at least one acoustic duct receiving respiratory air flow from the patient. A sensor is exposed to the acoustic duct and senses turbulence and/or vibration and/or sound in the air flow in the acoustic duct to provide an electric output signal. The electrical signal is digitally processed to provide a real-time signal indicative of breathing of the patient.

28 Claims, 2 Drawing Sheets

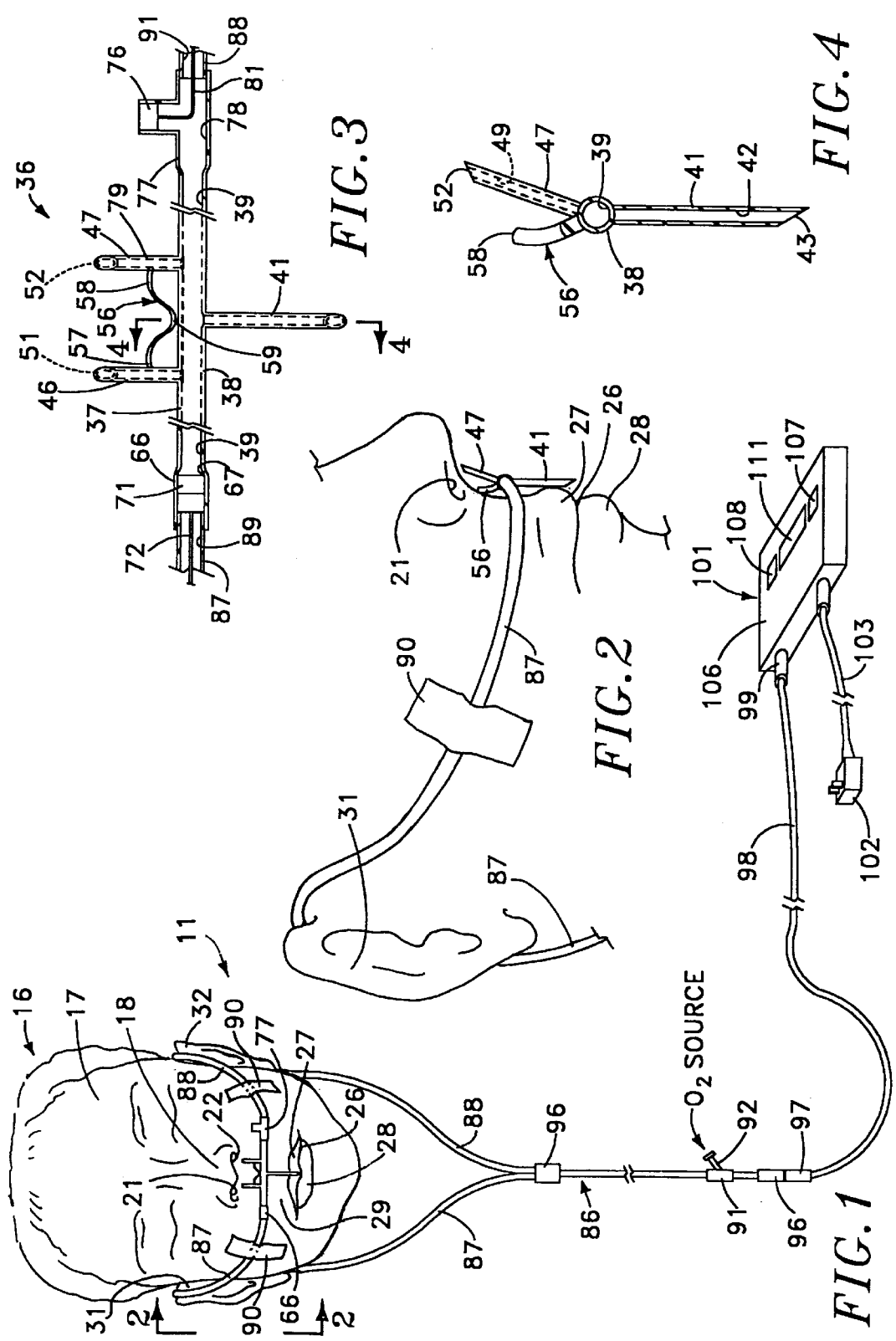

APPARATUS AND METHOD FOR BREATH MONITORING

This invention relates to an apparatus and method for breath monitoring.

Attempts have heretofore been made to monitor breathing with various types of devices. Certain of such devices have used thermocouples which depend on heating of the air as one exhales or cooling of the air as one inhales. These have generally been unsatisfactory because of the very long time constants associated with their reaction to breathing. An indirect method is using a pulse oximeter that measures breathing indirectly by measuring oxygen saturation in the blood. Oxygen saturation is a measure of $O_2$ binding to hemoglobin and typically is denoted by $SaO_2$. $SaO_2$ is determined by sending an optical signal in two wavelengths. Hemoglobin is a molecule, binding $O_2$. Since hemoglobin's light wavelength is a function of its oxygen saturation, oxygen saturation measurements are based upon sending an optical signal and determining the hemoglobin's wavelength according to the reflected signal. Determining breathing disorders by measuring oxygen saturation has several important shortcomings. The pulse oximeter is unable to differentiate the saturating gas. In other words, the pulse oximeter readings are the same for either blood which is saturated with $O_2$ or CO. The $SaO_2$ response is delayed. Thus for a person experiencing respiratory disorders like sleep apnea, a relatively long period of time such as two hours is required for the oxygen saturation to decrease. A pulse oximeter also does not work reliably when the patient's body is cold or the patient is just coming out of anaesthesia administered for surgery. In addition all these devices have the shortcomings in that they are incapable of accurately measuring air flow volume. There is therefore a need for a new and improved apparatus and method for breath monitoring and for measuring respiratory air flow.

In general, it is the object of the present invention to provide an apparatus and method for providing real-time breath monitoring and respiratory air flow.

Another object of the invention is to provide an apparatus and method of the above character in which the breath is directly monitored.

Another object of the invention is to provide an apparatus and method of the above character in which the breath is monitored by picking up the sound of breathing by the use of a microphone.

Another object of the invention is to provide an apparatus and method of the above character to monitor breathing by sensing vibrations caused by turbulence in the air flow.

Another object of the invention is to provide an apparatus and method of the above character in which the sound and vibration sensor work accurately with relatively low signal strengths.

Another object of the invention is to provide an apparatus and method of the above character in which disordered breathing can be readily ascertained.

Another object of the invention is to provide an apparatus and method of the above character which is operative even though the patient is being administered oxygen.

Another object of the invention is to provide an apparatus and method of the above character which can function in a noisy environment.

Another object of the invention is to provide an apparatus and method which can be utilized for monitoring breathing.

Another object of the invention is to provide an apparatus and method of the above character in which the information being generated can be transmitted to a remote location.

Another object of the invention is to provide an apparatus of the above character which is light in weight and easy to use and easy to apply and remove.

Additional objects and features of the invention will appear from the following description in which the preferred embodiments are set forth in detail in conjunction with the accompanying drawings.

FIG. 1 is a front elevational view of an apparatus incorporating the present invention mounted on the face of a human being or a patient.

FIG. 2 is a side elevational view looking along the line 2—2 of FIG. 1 showing the acoustical device as it is positioned on the face of the patient.

FIG. 3 is a rear elevational view of the acoustical device shown in FIG. 1.

FIG. 4 is a cross-sectional view taken along the line 4—4 of the acoustical device shown in FIG. 3.

Figure 5:
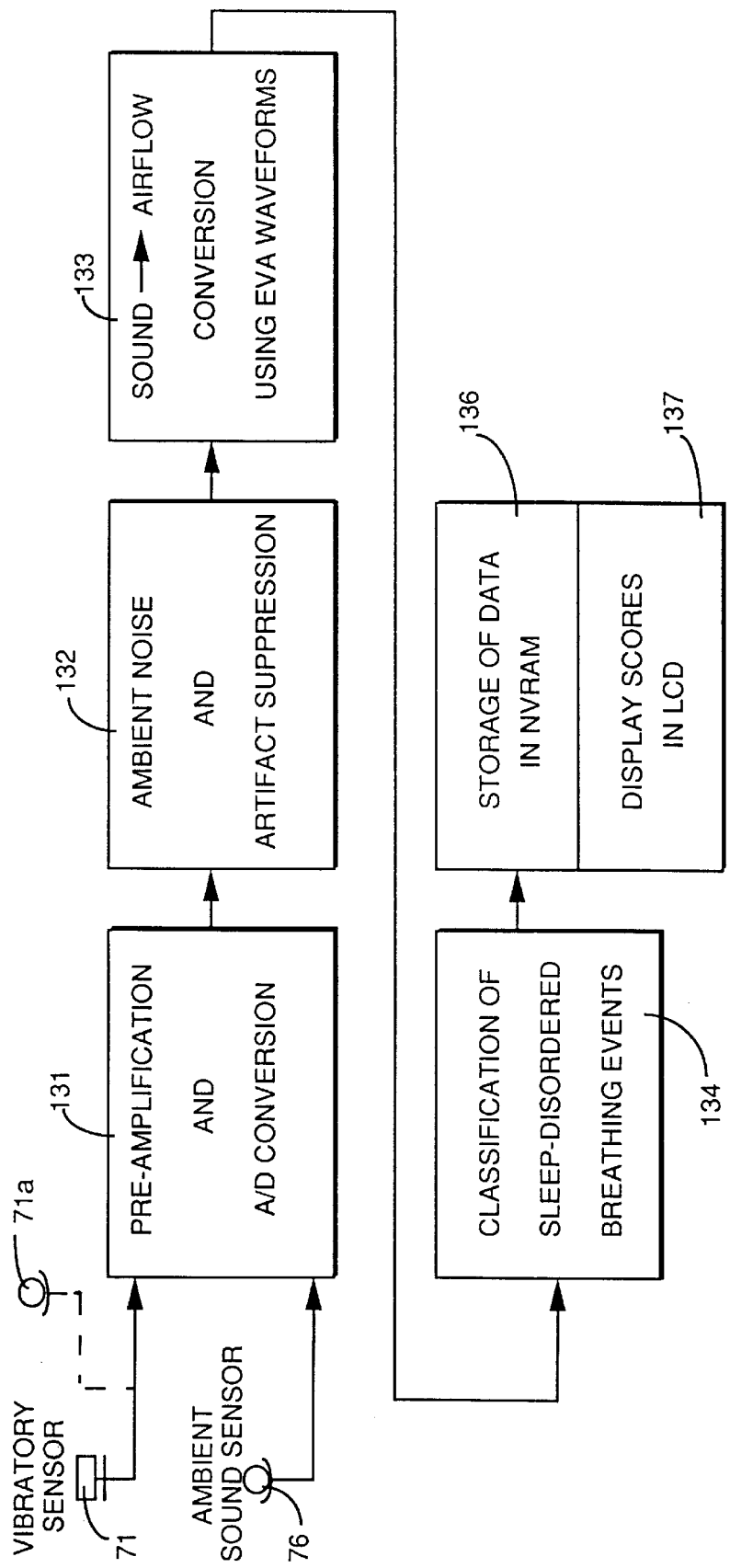
FIG. 5 is a block diagram of the electrical circuitry utilized in the apparatus for breath monitoring incorporating the present invention.

In general, the apparatus for breath monitoring monitors respiratory air flow from the nostrils of the nose and/or the mouth of the face of a patient and comprises an acoustical device positioned on the face of the patient in the vicinity of the nose and/or mouth of the patient and having at least one acoustic duct receiving respiratory air flow from the patient. A sensor is provided which is exposed to the acoustic duct and senses turbulence and/or pressure changes in the respiratory air flow in the acoustic duct and provides an electrical output signal. Means is provided for digitally processing the electrical output signal to provide a real-time signal indicative of breathing of the patient.

More in particular, the apparatus 11 for breath monitoring as shown in FIG. 1 is depicted as being used on a patient in the form of a human being having a head 16 having a centrally disposed nose 18 with first and second nostrils 21 and 22 which open downwardly over a mouth 26 formed by upper and lower lips 27 and 28. As shown, the upper lip 27 is positioned below the nostrils 21 and 22 so that there is provided a space 29 to be utilized for a purpose hereinafter described. The head 16 has ears 31 and 32 on opposite sides of the head 16.

The apparatus 11 includes an acoustic device 36 which is formed of a suitable medical grade plastic such as polyurethane, polyvinyl chloride and silicone. The acoustic device 36 is sized so that it is adapted to be mounted on the face 17 of the patient immediately below the lower extremity of the nose 18 and just above the upper lip 27 in the space 29. As shown, the acoustic device 36 can be formed of a single body of material which is relatively flexible so that it can accommodate the contours of the face so that it is comfortable while being worn by the patient.

The body 37 consists of an elongate tubular portion 38 which is generally disposed in a horizontal position on the face 17 as hereinafter described and is provided with an acoustic passage 39 extending therethrough. The body 37 is also provided with a tubular portion 41 which extends from the tubular portion 38 and extends at substantially right angles thereto. It is provided with an acoustic passage 42 extending therethrough and is in communication with the acoustic passage 39. The acoustic passage 42 opens through inclined cut or surface 43 provided on the tubular portion 41 which is inclined rearwardly and upwardly of the acoustic device 36. The body 37 is also provided with spaced apart upstanding tubular portions 46 and 47 which are inclined forwardly with respect to the vertical axis of the tubular portion 41 and are positioned so that they are equidistant sidewise with respect to the depending tubular portion 41. The tubular portion 41 has a length, so that when the acoustic device 36 is positioned on the face of the patient as hereinafter described, so that the inclined surface 43 is generally in alignment with the mouth 26 and is exposed to air flow into and out of the mouth 26. The tubular portion 41 typically can have a length ranging from ½" to 1" and preferably approximately ¾". Similarly, the upstanding tubular portions 46 and 47 have a length so that they immediately underlie the nostrils 21 and 22 of the patient when the acoustic device 36 is positioned on the face of the patient as hereinafter described. Thus they can have a length ranging from ⅛" to ½" and preferably approximately ¼". The upstanding tubular portions 46 and 47 have acoustic passages 48 and 49 extending therethrough which are in communication with the acoustic passage 39 in the elongate tubular portion 38. The acoustic passages 48 and 49 open through inclined surfaces 51 and 52 provided on the outer or uppermost extremities of the upstanding portions 46 and 47.

An elongate solid but yieldable support member 56 is formed integral with the body 37 and is formed of the same material as the body 37 and is generally quite flexible. As shown particularly in FIG. 4, it extends upwardly and rearwardly from the elongate tubular portion 38 for a distance of approximately one-half inch. As shown the support member 56 extends at a suitable angle as for example from 10° to 20° and preferably at an angle of approximately 20°. As shown particularly in FIG. 3 it can be provided with spaced-apart upwardly facing curved surfaces 57 and 58 with a curved surface 59 extending therebetween.

An adapter 66 is mounted on tubular portion 38. Alternatively as shown, this adapter 66 can be formed integral with the tubular portion 38. This adapter 66 is provided with an acoustic chamber 67 in communication with the acoustic passage 39. A sensor 71 is mounted in the acoustic chamber 66 and has a surface which is exposed to the acoustic passage 39 and is provided for sensing turbulence and/or pressure changes in the acoustical chamber 67 in communication with the acoustic passage 39 and provides an electrical signal on electrical conductors 72 connected to the sensor 71. The sensor 71 can be a vibration sensor or a microphone. The sensor 71 since it is exposed to the acoustic passage 39 will sense the vibrations and pressure changes generated by turbulent air flow within the acoustic passage 39.

In order to accommodate the needs of hospital environments and even in certain home environments, it is desirable to be able to provide the patient with oxygen in the event that this is required by the patent. Thus the acoustic device 36 can be used in much the same way as a nasal cannula conventionally utilized for delivering oxygen to a patient.

In order to increase the accuracy of the apparatus for breath monitoring, it is desirable to provide another sensor 76 for suppressing ambient sounds or noises in the vicinity of the patient. For this purpose, another tee-shaped adapter 77 is mounted on the other end of the tubular portion 38 opposite the end on which the adapter 66 is mounted. It can be a separate part or it can be formed integral with the tubular portion 38. It provides an acoustic chamber 78 which is in communication with the acoustic passage 39 and which opens into a centrally disposed leg 79. The sensor 76 is mounted in the leg 79 and is in the form of a microphone and is utilized for sensing ambient sounds and/or noise in the vicinity of the patient. The sensor 76 is connected to conductors 81 extending from the leg 79.

When it is desired that the apparatus 11 be versatile enough so that it can administer oxygen to the patient at the same time that breath monitoring is taking place, an oxygen tube set 86 is used. It consists of first and second tubes 87 and 88 which are connected to a wye adapter 91. The wye adapter 91 is provided with a side arm 92 which is connected to a suitable source of oxygen shown as "O₂ SOURCE" as for example an oxygen supply from the hospital piping or alternatively from a compressed oxygen container through an appropriate regulator apparatus (not shown). Oxygen is thereby supplied to both of the tubes 87 and 88 and which extend through a slip ring 96 slidably mounted on the tubes 87 and 88. The tubes 87 and 88 branch out in a wye in opposite directions and extend over the ears 31 and 32 of the patient and are connected to the adapters 66 and 77. If necessary, to additionally secure the tubes 87 and 88 in close contact on the face, pieces 90 of adhesive tape can be used as shown.

Since the sensor 71 is positioned within the adapter 66, oxygen will only be supplied through the other flexible tube 88 into the adapter 77 and thence into the upstanding tubular portions 46 and 47 as hereinafter described. The sensor 71 when oxygen is being delivered to the patient will also sense the constant oxygen flow which will also act as a disturbance signal contributing to the turbulence and pressure changes in the chamber 67. In such an arrangement, the conductor 72 will extend through the flow passage 89 and the tube 87. The conductors 81 will extend through the flow passage 91 of the tube 88 through the wye adapter 91 and into electrical coupling 96 which mates with another electrical coupling 97 to provide a disconnect between the oxygen tubing and electrical cable 98 which is connected to the coupling 97. The other end of the cable 98 is connected to a plug-in jack 99. The jack 99 as shown is plugged into a console 101 which is a sleep-disorder breathing detection device utilizing advanced audio digital signal processing technology as disclosed in co-pending application Ser. No. 08/472,441, filed Jun. 7, 1995, now U.S. Pat. No. 5,797,852. As described therein, the device is typically intended for unattended home studies of obstructive sleep apnea which has been designed to be simple to use, low cost and a non-invasive device with screening system accuracy. Typically the device calculates and stores some of the vital statistical information: time and duration of apneas and hypopneas, respiratory sound intensity, duration of patient snoring and respiratory disturbance index.

The console 101 houses a digital signal processor chip as well as memory and analog input preamplification circuitry which is powered from a conventional source of power such as 110 volts AC by use of a plug-in adapter 102 connected by a power cord 103 to the console 101. The console is provided with an inclined front panel 106 having provided thereon a start button 107, a stop button 108 and a back lit display 111. Typically the information provided by the display 111 includes a bar graph whose length is proportional to a snoring sound intensity and the following:

D—sleep study date
T—24 hour running system clock reference
ST—sleep study start time
ET—sleep study end time
TH—total breath monitoring study time minus study pauses (if any)
DBE—cumulative disordered breathing events during study
AHI—apnea hypopnea index; average number of DBE's per hour When the patient is ready to sleep, the start button 107 is pressed. The next morning the patient presses the stop button 108 to end the breath monitoring study.

The electrical circuitry which is utilized in the apparatus and method for breath monitoring is shown in block diagram form in FIG. 5. As shown in FIG. 5, the sensor 71 is a vibration sensor whereas the alternative sensor 71a is a microphone. Let it be assumed that the acoustic device 36 has been mounted on the face of the patient in the manner shown in FIG. 1 in which the oxygen tubes 87 and 88 are looped over the ears 31 and 32 and that the acoustic device has been positioned so that it is between the upper lip and nose as shown with the bottom extremity of the tubular portion 41 being in front of the mouth 26 between the upper and lower lips 27 and 28 of the patient and at the same time that the support member 56 rests against the upper lip of the patient in such a manner so that the upward extending tubular portions or canula 46 and 47 immediately underlie the nostrils 21 and 22 of the patient as shown in FIGS. 1 and 2.

Let it also be assumed that the oxygen tube set harness 86 is connected to an oxygen source and is also connected to the control console 101. The breathing monitoring study is now ready to be undertaken. By utilizing a vibration sensor as shown in FIG. 5, the vibration sensor 71 should be relatively immune to ambient sounds and should only be sensing the turbulence and pressure changes occurring in the acoustic passage 39 created by the patient breathing through the nostrils 21 and 22 of the nose 18 and/or through the mouth 26 with the air passing to and from the mouth being sensed by the extending tubular portion 41 and the air flow into and out of the nostrils being sensed by the canula or upwardly extending portions 46 and 47 of the body 37 of the acoustic device 36.

In order to obtain a greater accuracy in the breath monitoring, and particularly where noisy environments are encountered, an ambient sound sensor in the form of a microphone 76 is utilized to pick up the sound. The ambient sound sensor typically is in close vicinity to the face of the patient and the vibration sensor 71 as for example as being located on the other end of the acoustic device 36 as shown in FIG. 3. When oxygen is being supplied to the patient, the constant oxygen flow is measured in a conventional manner. The flow of oxygen will affect the turbulence and pressure changes occurring within the acoustic passage 39. In order to remove this constant flow oxygen signal, the ambient sound sensor or microphone 76 placed outside of the respiration area of the patient collects signals generated by the constant oxygen flow and also by ambient sounds and produces a signal which is proportional to the oxygen flow which is used to minimize the effect of the oxygen flow in the respiratory air flow to the patient. In connection with the foregoing it should be appreciated that the ambient sound sensor 76 should be isolated from the vibration sensor 71 in order to minimize acoustical coupling.

In the present invention by placing the sensor 71 in an acoustical chamber 67 which is in communication with acoustical ducts 39, 42, 48 and 49, the sensor 71 is measuring pressure changes and turbulence in the air flow as well as measuring sound. In addition, it has been found very desirable to at the same time that air flow measurements are being made to also measure respiratory sounds of the same patient or in other words ambient sounds in the vicinity of the nose and mouth of the patient by the use of the second sensor or microphone 76. Thus breathing sounds and snoring by the patient can be picked up by this second microphone 76 as well as other ambient noise. This microphone 76 acts as a respiratory sound sensor which is dedicated to sense the sound intensity in dB. It is placed outside of the air stream or streams created by the breathing of the patient in order to avoid the turbulence and vibrations generated by direct exposure to air flow. Thus, the second sensor is a proximity microphone predominantly receiving respiratory sounds but also receiving ambient noise.

The turbulence sensor microphone 71 and the ambient sound sensor 76 should be carefully positioned so that the acoustical and mechanical coupling between them is minimized. Thus the signal and noise components at the output of the vibratory sensor 71 are uncorrelated but the noise at the output of the respiratory sound sensor 76 is correlated with the noise component of the sensor 71 when a microphone is used.

The electrical circuitry in the console 13 is that which is disclosed in co-pending application Ser. No. 08/472,441 filed on Jun. 7, 1995, now U.S. Pat. No. 5,797,852. The circuitry pre-amplifies and A to D converts the signals received from the sensor 71 and the ambient sensor 76 in the form of dedicated sensors. These sensors supply analog signals which are amplified by analog preamplifiers and fed to A/D converters to an active noise canceler which contains an adaptive filter that uses the ambient sound sensor 76 as a reference to produce an estimate of the ambient noise which is subtracted from the primary sensor 71 output as represented in block 131. The output of the active noise canceler is used to adjust the tap weights in the adaptive filter. The adaptive filter minimizes the mean-square value of the overall output thereby causing the overall output to be the best estimate of the desired signal in the minimum-mean-square sense.

Efficient ambient noise suppression in the present invention is accomplished by developing a model for the acoustical transfer function of the space interconnecting the two sensors. The model employed in the present invention is in the form of a transversal filter consisting of a set of delay line elements each of which is represented by one sampling period of delay and a corresponding set of adjustable coefficients. At the sampling time instant, k, the available signal consists of a set of samples $$u(k), u(k-1), u(k-2) \ldots u(k-n) \tag{1}$$

These samples are convolved with a corresponding set of adjustable tap weights $$\omega_0, \omega_1, \omega_2, \ldots, \omega_n$$

to produce an output signal sequence, y(n) with the signal collected by the ambient noise sensor 76 being d(n). The filter output y(n) is compared with the d(n) to produce an estimation error e(n) which is used by the adaptive algorithm whereby it controls the corrections applied to the individual tap weights. This procedure is continued until the noise estimation error e(n) becomes sufficiently small in order to encounter the possible directions of arrival to the sensors. To keep the estimation algorithm casual during its operation, an internal time delay of d is added to the reference input signal. The time duration of d is selected according to the sampling rate and the assumed distance between the two microphones.

For a sampling rate of 8000 Hz and a distance of 1 cm between the two microphones, the sound propagation delay is about $$T = \frac{d}{c} = \frac{1\,\text{cm}}{320\,\text{m/s}} = 31.25\ \text{microseconds} \tag{2}$$

Should the acoustical properties of the testing environment change, the adaptive algorithm used to adjust the coefficients has the added task of continually tracking the variations of the system. For this reason a normalized adaptation step size has been used to improve the convergence rate.

The electrical circuitry in the console 101 also includes a band-pass filter bank consisting of several narrow band-pass filters as described in co-pending application Ser. No. 08/472,441 filed Jun. 7, 1995, now U.S. Pat. No. 5,797,852, which information is incorporated herein by reference. The software performs an appropriate selection of a frequency band in order to improve the sound digital quality, i.e., reduce any interference of ambient noise. The task of this software module is to determine a frequency band where the signal-to-noise ratio for a given turbulence or vibration is maximum. In general, the useful portion of the sensor frequency spectrum is within the frequency band of 100 Hz to 1500 Hz. The filtering section consists of ten filters each having a band width of 300 Hz and having cutoff frequencies from 200 Hz to 1500 Hz.

When the signal from the active noise canceler reaches the band-pass filter it is applied to each of the ten filters and corresponding outputs are computed. Since the input signals are known, the filter that yields the best signal-to-noise ratio is selected and used for each successive three-minute period. At the end of each three-minute period, the selection process is repeated in order to compensate for any possible variations in the vibration or turbulence characteristics.

The filters in the console 101 are realized by using Butterworth's technique. These filters have a flat response in the pass-band and are monotonic overall. The filter is of autoregressive-moving average type, having both poles in zero so that as sharp as possible attenuation rate is obtained with a minimum number of taps. The 3rd order Butterworth type filter output y(k), can be described by $$y(k)=a_1 y(k-1)+a_2 y(k-2)+ \ldots +a_6 y(k-6)+b_0 u(k)+b_1 u(k-1)+ \ldots +b_6 u(k-6) \quad (3)$$

For this application, all the $a_i$ and $b_i$ coefficients are calculated by using the Matlab routine

[numerator, denominator]=Butter(filter order, cutoff frequencies)

This ambient noise and artifact suppression hereinbefore described is set forth in box 132 of FIG. 5. This step is followed by a step of sound/air flow conversion utilizing EVA waveforms as set forth in box 133 in FIG. 5. If sensors 71 and 76 are both microphones, the sensor 71a receives respiration plus $O_2$ flow signals whereas the second sensor 76 receives predominantly $O_2$ flow. The ambient sounds are received by both microphones 71a and 76. Therefore a suitable subtraction of sensor 76 signals from sensor 71a signals improves the quality of the breathing or respiration signals being obtained. As pointed out previously since the sensors 71a and 76 are not co-located, the analysis heretofore given must take into account the acoustical transfer function between the sensors 71a and 76. Thus the signals received from the box 132 are converted to air flow signals utilizing the EVA transformation shown in block 133.

In order to determine whether the patient's breathing is disordered, the amount of air volume inhaled and exhaled needs to be known. The microphone signal which is available after the steps shown in box 132 have been performed still are not very informative as to air flow volume. In other words even though the sound signal contains the required air flow volume information the sound signal at this point does not directly provide it. For this reason and in accordance with the present invention the waveform is generated and a scoring methodology is utilized for this waveform that closely mimics the results of the core of a conventional scoring mechanism using a standard polysomnograph. If desired, the waveforms generated can be displayed on a CRT to permit viewing or visual inspection by a skilled technician. The signal after it has been subjected to the steps shown in box 132 is subjected to a process where it is converted to an estimated volume of air flow (EVA) waveform that represents an estimate of its acoustical energy. This conversion procedure, which is explained in application Ser. No. 08/472,441 filed Jun. 7, 1995, now U.S. Pat. No. 5,797,852, is performed digitally in a discrete time domain and is somewhat similar to a high order integration process in a continuous-time domain. In accordance with the present invention, the following prediction sequence is utilized for generating the estimated volume of air flow waveforms that are expected to closely follow the actual air volume that is inhaled or exhaled by the patient. The software code implements the following equation for this purpose.

$$\sigma(k)=\alpha_1 \sigma(k1)+\alpha_2 \sigma(k2)+\alpha_3 \sigma(k3)+ \ldots +\alpha_m \sigma(k/m)+\beta|x(k)| \quad (4)$$

where $\alpha$ and $\beta$ are user defined parameters that change the shape of the waveforms. It is found that $\alpha_1=0.995$, $\alpha_i=0.0$ for i=2, 3, . . . , m and $\beta=0.2$ were suitable choices for obtaining a waveform that closely resembles air flow waveforms that are obtained by using the standard polysomnograph. To obtain a condition for stability, the z-transform of this equation yields $$(z-\alpha)\,\sigma(z)=\beta z X(z) \quad (5)$$

Then, $$\sigma(z)=\beta[z/(z-a)]X(z) \quad (6)$$

a selection of $$0<\alpha<1$$

is sufficient to obtain stability for the algorithm.

The next which follows the step shown in box 133 are steps shown in box 134 for the classification of disordered breathing events.

As hereinbefore pointed out, once a respiration sound has been sensed by the respiratory sound sensor 71 or 71a it must be processed to ensure that it is indeed a breath pattern. After that has been ascertained, its characteristics can be analyzed to detect disordered breathing. Since these parameters are mostly patient-dependent, a set of self-tuning algorithms that characterize a given breath signature are utilized. This has been accomplished by utilizing intermediate variables in the form of the estimated volume of air flow (EVA) waveforms hereinbefore described and thresholds to obtain a very close scoring correlation with that of the standard polysomnograph. At the same time, if desired, the frequency of breathing can be ascertained.

As explained in co-pending application Ser. No. 08/472, 441 filed on Jun. 7, 1995, now U.S. Pat. No. 5,797,852, a pattern classifier is utilized for operating on the EVA waveforms which is a rule-based decision making unit. It operates on the EVA waveforms for the determination of disordered breathing events by employing a set of time-varying coefficients that are designed to adapt to a given breathing pattern. The related set of parameters are adjusted to score an event when the cessation of a less or less than normal air flow levels have been encountered for a duration of ten seconds or longer. The less than normal definition that has been followed applies to an air flow reduction by 50% relative to nominal levels. For a classification, a time-varying nominal value is first assigned by detecting peaks of the EVA waveform. Based on this value, the apnea threshold for the determination of less than normal breathing levels is computed. The remainder of the EVA waveform is then monitored to detect any events taking place.

After the classifications called for in the block 134 have been accomplished, the information is stored in a memory of a suitable type and the sleep-disordered breathing events occurring can be displayed in an LCD shown by the box 137 much in the same manner as described in co-pending application Ser. No. 08/472,441 filed on Jun. 7, 1995, now U.S. Pat. No. 5,797,852, or alternatively on a CRT for visual observation.

Also in accordance with the present invention, once a signal has been received after the pre-amplification A/D data conversion as represented by the box 131, additional information can be obtained without any hardware changes. Thus it is possible to readily provide information on sound level intensity. This is accomplished by utilizing the information supplied by the ambient sound sensor 76 which picks up the sound field which may include respiratory sounds. In accordance with the present invention, this signal is sampled at 5.525 kHz rate. A plain logarithmic conversion provides sound levels in decibels (dB). A plain logarithmic conversion is identified as $dB_c$. Where human perception is involved, especially below 1000 Hz, another decibel scale has been developed identified as $dB_A$. Thus in accordance with the present invention, the console 101 is utilized to calculated $dB_A$ by digitally weighting the frequencies below 1000 Hz so that the characteristics closely match that of published $dB_A$ curves.

For a direct conversion from the signal after the box 131, $dB_c$ is computed with the collected sensor signal being noted by x(t) and its logarithmic correspondent y(t) is $$y(t) = 20 \log_{10}\{s(t)/S_{ref}\}; \quad (7)$$

and $$s(t) = f[\Sigma \ x(t)]$$

where f(p) is a function that performs a frequency waiting over a collected time window samples and s is the reference.

The $dB_A$ conversion process is performed by a well-parameterized software code to provide flexibility to address different needs. In connection with the present invention, the console 13 makes $dB_A$ measurements five times per second and stores. After collecting one minute long $dB_A$ data, minimum peak dB, maximum peak dB and one-minute windowed average (two 300 samples) dB values are transferred to the processor memory. At the end of the study, along with other disordered breathing information and statistics, the dB level information containing minimum, maximum and average value measurements at every minute are stored into the non-volatile random access memory (NVRAM). The dB measurement is calibrated by using an accurate meter from the ambient noise floor (approximately 40 $dB_A$) to 110 $dB_A$ at every five $dB_A$ intervals.

From the foregoing description from the use and operation of the apparatus in performing the method of the present invention, the following sequence events are utilized.

1. Turbulence and vibration in respiratory air flow sounds as well as ambient sounds are picked up by the dedicated sensors
2. The signal quality is improved and noisy components are removed by a filter bank
3. The purified air flow sound signal is converted to an air flow curve called EVA
4. Based on the EVA waveforms, disordered breathing events are identified
5. Apnea and hypopnea events are classified
6. The purified respiratory sound signal is used to calculate the sound intensity level (dB)
7. The display is updated
8. The data are stored in an internal non-volatile random access memory (NVRAM) chip
9. Display on a CRT
10. Initiate alarm in the event of abnormal breathing From the foregoing it can be seen that an apparatus and method has been provided for breath monitoring which provides a more accurate means for recognizing disordered breathing patterns and for providing respiratory sound intensity. The apparatus has built-in operational intelligence and has been designed to make the apparatus have a simple appearance and so that it can function reliably in a home environment and at the same time be user friendly. Thus time and duration of apneas and hypopneas can be readily classified into events. At the same time sound intensity levels can be displayed at every three minutes. Sufficient storage capacity is provided so that four ten-hour breath monitoring studies can be retained. A Windows®-based software code makes it possible to retrieve, display and print the collected data on a personal computer platform. A summary report and event log are provided for reviewing the sleep data quoted.

Although the apparatus and method have been principally described in conjunction with real-time studies for disordered breathing in adults, it should be appreciated that the apparatus and method can also be utilized for monitoring small infants for monitoring their breathing non-invasively. The apparatus and method can also be utilized for monitoring the performance of athletes and how they react under stress. By utilizing radio frequency telemetry as hereinbefore described, the athletes can be monitored even when they are on the athletic field or doing workouts. Conventional wireless methods may be utilized for conveying the information to the desired site. In addition, the apparatus and method can be utilized for monitoring the breathing of patients undergoing anesthesia and other medical procedures.

When oxygen is being administered to the patient at the same time that breathing of the patient is being monitored, the active noise cancellation requires the implementation of a notch filter type response to suppress tonal natured noise due to constant oxygen flow to the patient. This makes it necessary to model the transfer function for the acoustic path between the two sensors so that ambient sounds are canceled.

From the foregoing it can be seen that the apparatus and method of the present invention makes it possible to ascertain relative air flow levels continuously, ascertaining breathing frequency in breaths per minute to establish the breathing form and to alarm when a breath pattern is found to be disordered.

What is claimed is:

1. Apparatus for breath monitoring by sensing respiratory air flow from the nostrils of the nose and/or the mouth of the face of a patient comprising an acoustical device for receiving less than the actual air volume exhaled and inhaled adapted to be positioned on the face of the patient in the vicinity of the nose and/or mouth of the patient and having at least one acoustic space adapted to receive respiratory air flow from the patient, a change sensing sensor exposed to the acoustic space for sensing turbulence and/or pressure changes and/or sound in the respiratory air flow in the acoustic space and providing an electrical output signal serving as the sole means for sensing respiratory air flow from the patient and means for processing the electrical output signal including means for providing an estimated volume of air flow to provide a real-time signal indicative of breathing of the patient.

2. Apparatus for breath monitoring by sensing respiratory air flow from the nostrils of the nose and/or the mouth of the face of a patient comprising an acoustical device for receiving less than the actual air volume exhaled and inhaled adapted to be positioned on the face of the patient in the vicinity of the nose and/or mouth of the patient and having at least one acoustic space adapted to receive respiratory air flow from the patient, a change sensing sensor exposed to the acoustic space for sensing turbulence and/or pressure changes and/or sound in the respiratory air flow in the acoustic space and providing an electrical output signal, means processing the electrical output signal including means for providing an estimated volume of air flow to provide a real-time signal indicative of breathing of the patient, means coupled to said space for introducing a flow of oxygen into said space for supplying oxygen to the patient and an ambient sensor in communication with said space but spaced away from said change sensing sensor to minimize acoustical and mechanical coupling, said ambient sensor being exposed to the flow of oxygen into said space producing an electrical output a signal which is proportional to the flow of oxygen which is combined with the electrical output signal from the change sensing sensor to minimize the effect of the oxygen flow in sensing the respiratory air flow into the patient.

3. Apparatus as in claim 1 wherein said change sensing sensor is a vibratory sensor.

4. Apparatus as in claim 1 wherein said change sensing sensor is a microphone.

5. Apparatus for breath monitoring by sensing respiratory air flow from the nostrils of the nose and/or the mouth of the face of a patient comprising an acoustical device for receiving less than the actual air volume exhaled and inhaled adapted to be positioned on the face of the patient in the vicinity of the nose and/or mouth of the patient and having at least one acoustic space adapted to receive respiratory air flow from the patient, a change sensing sensor exposed to the acoustic space for sensing turbulence and/or pressure changes and/or sound in the respiratory air flow in the acoustic space and providing an electrical output signal, means processing the electrical output signal including means for providing an estimated volume of air flow to provide a real-time signal indicative of breathing of the patient, an additional sensor in the form of a microphone adapted to be positioned in the vicinity of the nose and/or mouth of the patient and out of communication with the acoustic space for measuring ambient sounds including respiratory sounds in the vicinity of the nose and/or mouth and providing an electrical output signal, means combining the output signals from the first named and additional sensors for reducing ambient noise signals from the signal of the first-named sensor and means utilizing the combined electrical output signals for recognizing disordered breathing patterns.

6. Apparatus as in claim 5 further including means coupled to the combined output signals for providing a measure of respiratory sound intensity.

7. Apparatus as in claim 6 wherein said measured respiratory sound intensity is in the form of $dB_A$.

8. Apparatus as in claim 7 wherein said means for providing respiratory sound intensity includes means for displaying the sound intensity at predetermined time intervals.

9. Apparatus as in claim 1 wherein said acoustical device is comprised of a body having an elongate portion having a length and width so as adapted to fit underneath the nose of the patient and on the upper lip of the patient, wherein said acoustical space is disposed in the body and wherein said sensor is in communication with said acoustical space, said body having a plurality of ports therein exposed to respiratory flow and in communication with the acoustical space.

10. Apparatus as in claim 9 wherein at least certain of said ports are adapted to underlie the nostrils of the nose.

11. Apparatus as in claim 9 wherein said body of said device includes a portion adapted to extend over the mouth of the patient and having an acoustical duct therein in communication with the acoustical duct in the elongate portion, said body also having a port therein in communication with the acoustical duct in the portion adapted to overlie the mouth of the patient and adapted to face towards the mouth of the patient to monitor air flow into and from the mouth of the patient.

12. Apparatus as in claim 11 wherein said portion of the body adapted to overlie the mouth of the patient is in the form of a depending portion depending from the elongate portion.

13. Apparatus as in claim 1 further including means adapted to secure the device to the patient and including loops adapted to extend around the ears of the patient and secured to the body.

14. Apparatus as in claim 11 wherein said body includes at least one port adapted to underlie each of the nostrils of the nose and at least one port adapted to be opening in the vicinity of the mouth of the patient.

15. A method for measuring respiratory air flow from the nostrils of the nose and/or the mouth of a patient by the use of an acoustical device for receiving less than the actual air volume exhaled and inhaled by the patient and adapted to be positioned on the face of the patient and in the vicinity of the nose and/or mouth of the patient and having at least one acoustic space adapted to receive respiratory air flow from the patient comprising sensing turbulence and/or vibration and/or sound in the acoustic space and providing an electrical signal serving as the sole indication for respiratory air flow from the patient and processing the electrical signal to provide an estimated volume of air flow to provide a real-time indication of actual respiratory flow from the patient.

16. A method for measuring respiratory air flow from the nostrils of the nose and/or the mouth of a patient by the use of an acoustical device for receiving less than the actual air volume exhaled and inhaled by the patient and adapted to be positioned on the face of the patient and in the vicinity of the nose and/or mouth of the patient and having at least one acoustic space adapted to receive respiratory air flow from the patient comprising sensing turbulence and/or vibration and/or sound in the acoustic space and providing an electrical signal and processing the electrical signal to provide an estimated volume of air flow to provide a real-time indication of actual respiratory flow from the patient, sensing respiratory sounds and ambient noise in the vicinity of the face of the patient and providing an additional electrical output signal, combining the first named and additional electrical output signals to provide a combined signal which is substantially free of respiratory sounds and ambient noise and utilizing the combined signal to provide a real-time indication of actual respiratory air flow in which the effects of respiratory sounds and ambient noise have been minimized.

17. A method as in claim 16 further including the step of analyzing the combined signal using rule-based decision making to ascertain disordered breathing events.

18. A method as in claim 16 further including the step of utilizing the combined signal to provide an indication of respiratory sound intensity.

19. A method as in claim 18 wherein the respiratory sound intensity is provided in $dB_A$.

20. A method as in claim 15 further including the step of ascertaining the frequency of breathing.

21. A method as in claim 17 further including the step of displaying disordered breathing events.

22. A method as in claim 15 further including the step of analyzing the estimated volume of air flow using rule-based decision making for scoring a disordered breathing event.

23. A method as in claim 21 in which a disordered breathing event is scored when there is a cessation of normal air flow over a predetermined time.

24. A method as in claim 23 in which cessation of normal breathing is applicable when there is an air flow reduction by 50% relative to a nominal value for a period of 10 seconds or longer.

25. A method as in claim 22 in which apnea and hypopnea events are classified.

26. Apparatus for breath monitoring by sensing respirator air flow from the nostrils of the nose and/or the mouth of the face of a patient comprising an acoustical device for receiving less than the actual air volume inhaled and exhaled adapted to be positioned on the face of the patient in the vicinity of the nose and/or mouth of the patient and having at least one acoustic space adapted to receive respiratory air flow from the patient, a sensor exposed to the acoustic space for sensing turbulence and/or pressure changes and/or sound in the respiratory air flow in the acoustic space and providing an electrical output signal serving as the sole means for sensing respiratory air flow from the patient and means for processing the electrical signal including means for providing an estimated volume of air flow to provide in real time a signal indicative of actual air flow to and from the patient.

27. Apparatus for breath monitoring by sensing respirator air flow from the nostrils of the nose and/or the mouth of the face of a patient comprising an acoustical device for receiving less than the actual air volume inhaled and exhaled adapted to be positioned on the face of the patient in the vicinity of the nose and/or mouth of the patient and having at least one acoustic space adapted to receive respiratory air flow from the patient, a sensor exposed to the acoustic space for sensing turbulence and/or pressure changes and/or sound in the respiratory air flow in the acoustic space and providing an electrical output signal and including means for providing an estimated volume of air flow for processing the electrical signal indicative in real time of actual air flow to and from the patient, means for applying rule-based decisions to the estimated volume of air flow by employing a set of time varying coefficients adapted to a predetermined breathing pattern to provide a classified output and means utilizing the classified output in scoring an event upon cessation of normal breathing of the patient for greater than a predetermined period of time.

28. Apparatus as in claim 27 wherein said cessation of normal breathing is considered to occur when there is an air flow reduction by 50% relative to nominal values and in which a predetermined period of time is 10 seconds greater.

* * * * *